(12) United States Patent
Haase

(10) Patent No.: US 8,708,959 B2
(45) Date of Patent: Apr. 29, 2014

(54) DETECTING FILL STATUS FOR MEDICAL PUMP RESERVOIR

(75) Inventor: James M. Haase, Maplewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 127 days.

(21) Appl. No.: 13/081,860

(22) Filed: Apr. 7, 2011

(65) Prior Publication Data

US 2012/0259283 A1 Oct. 11, 2012

(51) Int. Cl.
*A61M 1/00* (2006.01)
*A61M 31/00* (2006.01)
*A61M 37/00* (2006.01)

(52) U.S. Cl.
USPC ............... 604/151; 604/93.01; 604/288.01

(58) Field of Classification Search
USPC .......................................... 604/151
See application file for complete search history.

(56) References Cited

U.S. PATENT DOCUMENTS

| | | | |
|---|---|---|---|
| 5,176,502 A * | 1/1993 | Sanderson et al. | 417/18 |
| 5,636,548 A * | 6/1997 | Dunn et al. | 73/313 |
| 2001/0034502 A1 | 10/2001 | Moberg | |
| 2006/0178633 A1 * | 8/2006 | Garibotto et al. | 604/155 |
| 2007/0255259 A1 * | 11/2007 | Miesel | 604/890.1 |
| 2010/0280501 A1 | 11/2010 | Young et al. | |

OTHER PUBLICATIONS

U.S. Appl. No. 61/174,457, "Modular Medical Pump", filed Apr. 30, 2009, 49 pgs.

* cited by examiner

*Primary Examiner* — Jason Flick
(74) *Attorney, Agent, or Firm* — Mueting, Raasch & Gebhardt, P.A.

(57) ABSTRACT

A medical device system comprises a reservoir configured to store a therapeutic fluid and a medical pump configured to deliver the therapeutic fluid from the reservoir to a patient. The system also comprises a reservoir fill level detector configured to detect a fill status of the reservoir, the reservoir fill level detector including a contact pad operably attached to the reservoir whereby the contact pad moves in a predetermined path during the emptying and filling of the reservoir. A resistor strip mounted on the inside of the chamber is in continual contact with the contact pad and the resistance of an electric current passed through the resistor strip is monitored by a processor to determine the position of a selected portion of the reservoir. The position of the reservoir is directly related to the fill status.

11 Claims, 6 Drawing Sheets

DETECTING FILL STATUS FOR MEDICAL PUMP RESERVOIR

TECHNICAL FIELD

The disclosure relates to implantable fluid delivery devices.

BACKGROUND

Implantable fluid delivery devices are used to treat a number of physiological, psychological, and emotional conditions, including chronic pain, tremor, Parkinson's disease, epilepsy, urinary or fecal incontinence, sexual dysfunction, obesity, spasticity, or gastroparesis. For some medical conditions, an implantable fluid delivery device provides the best therapy to restore a patient to a more healthful condition.

An implantable fluid delivery device typically provides a patient with a programmable infusion of a drug or other therapeutic agent. The fluid delivery device typically includes a reservoir for storing the therapeutic agent, a fill port, a pumping mechanism to pump the therapeutic agent from the reservoir, a catheter port to transport the therapeutic agent from the reservoir to a patient's anatomy, and electronics to control the pumping mechanism.

SUMMARY

In general, the disclosure relates to systems and methods of delivering a therapeutic fluid to a patient from a reservoir and to systems and methods for determining fill status.

The details of one or more embodiments of the disclosure are set forth in the accompanying drawings and the description below. Other features, objects, and advantages of the disclosure will be apparent from the description and drawings, and from the claims.

In one embodiment, the present invention includes a medical device system including a reservoir configured to store a therapeutic fluid, the reservoir positioned in a chamber, a reservoir fill level detector configured to detect a fill status of the reservoir, the reservoir fill level detector further including a contact pad operably attached to the reservoir whereby the contact pad moves in a predetermined path during the emptying and filling of the reservoir, a resistor strip mounted on the inside of the chamber whereby the resistor strip is in continual contact with the contact pad along the entire predetermined path, an energy source for providing a current along the resistor strip whereby the total resistance of the resistor strip is variable depending on the position of the contact pad, a processor configured to monitor the resistance of the resistor strip.

Another embodiment includes a reservoir fill level detector operably mounted relative to a reservoir attached in a housing of an implantable medical pump, a reservoir configured to store a therapeutic fluid, the reservoir positioned in the housing and including at least one surface moveable relative to the housing of the implantable medical pump, an inductive coil positioned relative to the reservoir, a lever arm hingedly attached relative to the reservoir in a predetermined position relative to the inductive coil whereby the lever arm moves in coordination with the moveable surface of the reservoir, and a magnetic block operably attached to the lever arm whereby filling and emptying the reservoir with therapeutic fluid causes the at least one surface of the reservoir to move such that the lever arm and the magnetic block are repositioned and the magnetic block is moved relative to the coil.

DETAILED DESCRIPTION

In general, this disclosure is directed to techniques for providing a medical device for the delivery of a therapeutic fluid with reservoir fill status detection. In one example, the medical device may include a reservoir configured to store a therapeutic fluid and a medical pump configured to deliver the therapeutic fluid from the reservoir to a patient. The pump may include an actuation mechanism configured to be energized to provide a pump stroke, such as an electromagnetic coil and an actuator that is movable in response to the coil being energized. The device also may include a sensor configured to detect a property associated with the fill status. In one embodiment the resistance of a circuit operably attached to the reservoir helps to determine the relative fill status. The device may also include a processor configured to determine the fill status based on the information provided by the circuit and rheostat. The amount of fluid in the reservoir is known when the reservoir is filled with the therapeutic agent. Alternative embodiment are further discussed in detail below.

As the therapeutic agent is pumped from the reservoir, the status of the fluid fill level may be updated. It may be important to know the refill status to indicate a low volume level to the patient or to check the accuracy of the pump by checking the calculated volume dispensed versus the actual volume dispensed. In addition, during a refill procedure, it may be helpful to know that the reservoir is receiving fluid to determine in real time if, for example, some of the therapeutic agent is being injected into the subcutaneous pocket in which the fluid delivery device was implanted, known as a "pocket fill."

Figure 1:
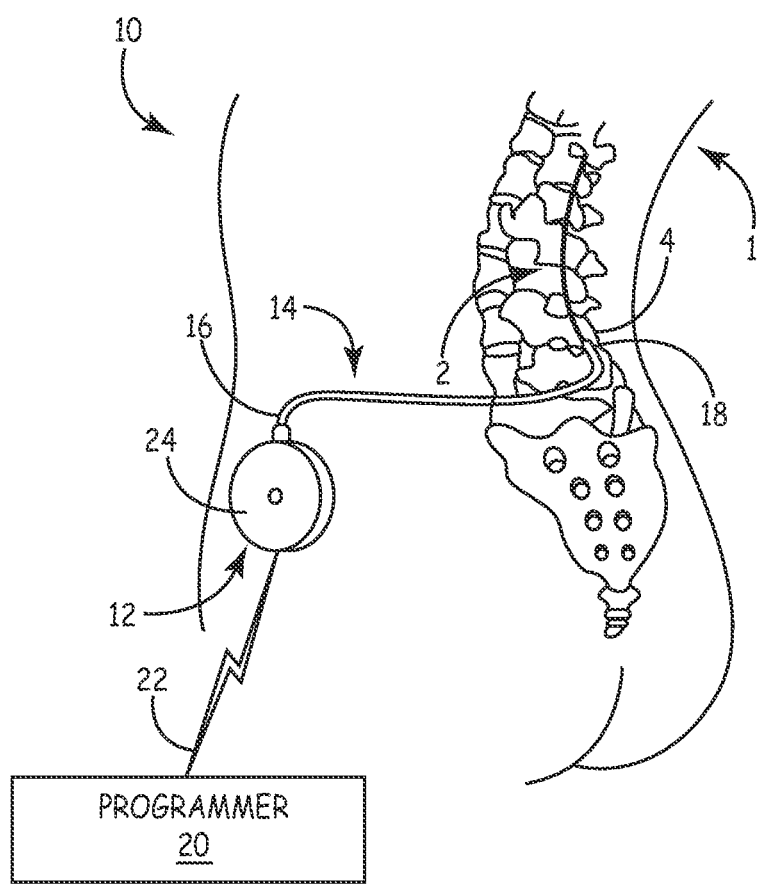
FIG. 1 is a conceptual diagram illustrating an example fluid delivery system.

FIG. 1 is a schematic diagram of an example system 10, including an implantable medical device (IMD) 12, which is configured to deliver a therapeutic agent, such as a pharmaceutical agent, for example a drug, insulin, pain relieving agent, anti-inflammatory agent, gene therapy agent, or the like, to a target site 2 within a patient 1. The therapeutic agent is delivered via a catheter 14 that is coupled to IMD 12. Catheter 14 may comprise a plurality of catheter segments, or catheter 14 may be a unitary catheter. In the example shown in FIG. 1, target site 2 is proximate to spinal cord 4 of patient 1.

A proximal end 16 of catheter 14 is coupled to IMD 12 while a distal end 18 of catheter 14 is positioned proximate target site 2. System 10 may also include an external programmer 20 that communicates with IMD 12 as needed, such as to provide or retrieve therapy information or other treatment parameters associated with therapy delivery. For example, external programmer 20 may be configured to turn IMD 12 on or off, to deliver the initial therapy parameters for patient 1, to modify the therapy parameters, and so forth. In one example, external programmer 20 communicates with IMD 12 wirelessly 22, as shown in FIG. 1.

Although patient 1 is generally referred to as a human patient in the present disclosure, system 10 can be used with other mammalian or non-mammalian patients. IMD 12 may be employed to treat, manage or otherwise control various conditions or disorders of patient 1, including, e.g., pain (e.g., chronic pain, post-operative pain or peripheral and localized pain), tremor, movement disorders (e.g., Parkinson's disease), diabetes, epilepsy, neuralgia, chronic migraines, urinary or fecal incontinence, sexual dysfunction, obesity, gastroparesis, mood disorders, or other disorders.

IMD 12 may be configured to deliver one or more therapeutic agents, alone or in combination with other therapies, including, e.g., electrical stimulation. For example, in some cases, a medical pump may deliver one or more pain-relieving drugs to patients with chronic pain, insulin to a patient with diabetes, or other fluids to patients with different disorders. Example therapeutic agents that IMD 12 may be configured to deliver include insulin, morphine, hydromorphone, bupivacaine, clonidine, other analgesics, genetic agents, antibiotics, nutritional fluids, analgesics, hormones or hormonal drugs, gene therapy drugs, anticoagulants, cardiovascular medications or chemotherapeutics. A therapy program, generally speaking, may set forth different therapy parameters, such as a therapy schedule specifying programmed doses, dose rates for the programmed doses, and specific times to deliver the programmed doses. IMD 12 may be implanted in patient 1 for chronic or temporary therapy delivery.

IMD 12 includes an outer housing 24 that is constructed of a biocompatible material that resists corrosion and degradation from bodily fluids, such as titanium or biologically inert polymers. IMD 12 may be implanted within a subcutaneous pocket close to target site 2. For example, as shown in FIG. 1, IMD 12 may be implanted within the abdomen of patient 1 close to the position along spinal cord 4 where target site 2 is located. In other examples, IMD 12 may be implanted within other suitable sites within patient 1, which may depend, for example, on where target site 2 is located within patient 1, and the ease of implanting IMD 12 within suitable locations near target site 2.

Catheter 14 may be coupled to IMD 12 either directly or with the aid of a catheter extension (not shown). In the example shown in FIG. 1, catheter 14 traverses from the implant site of IMD 12 to target site 2 proximate to spinal cord 4. Catheter 14 is positioned such that one or more fluid delivery outlets of catheter 14 are proximate to one or more locations within patient 1. In the example shown in FIG. 1, IMD 12 delivers a therapeutic agent to one or more locations at target site 2 within patient 1. IMD 12 delivers a therapeutic agent to target site 2 proximate spinal cord 4 with the aid of catheter 14. For example, IMD 12 may be configured for intrathecal drug delivery into the intrathecal space or epidural space surrounding spinal cord 4.

In some examples, multiple catheters may be coupled to IMD 12 to target the same or different tissue or nerve sites within patient 1. Thus, although a single catheter 14 is shown in FIG. 1, in other examples, system 10 may include multiple catheters or catheter 14 may define multiple lumens for delivering different therapeutic agents to patient 1 or for delivering a therapeutic agent to different tissue sites within patient 1. Accordingly, in some examples, IMD 12 may include a plurality of reservoirs for storing more than one type of therapeutic agent. However, for ease of description, an IMD 12 including a single reservoir is primarily discussed herein with reference to the example of FIG. 1.

Programmer 20 is an external computing device that is configured to wirelessly communicate with IMD 12. For example, programmer 20 may be a clinician programmer that the clinician uses to communicate with IMD 12. Alternatively, programmer 20 may be a patient programmer that allows patient 1 to view and modify therapy parameters. A clinician programmer may include additional or alternative programming features, relative to a patient programmer. For example, more complex or sensitive tasks may only be allowed by the clinician programmer to prevent patient 1 from making undesired changes to the operation of IMD 12.

Programmer 20 may be a hand-held computing device that includes a display viewable by the user and a user input mechanism that can be used to provide input to programmer 20. For example, programmer 20 may include a display screen (e.g., a liquid crystal display or a light emitting diode display) that presents information to the user. In addition, programmer 20 may include a keypad, buttons, a peripheral pointing device, touch screen, voice recognition, or another input mechanism that allows the user to navigate through the user interface of programmer 20 and provide input.

In other examples, rather than being a handheld computing device or a dedicated computing device, programmer 20 may be a larger workstation or a separate application within another multi-function device. For example, the multi-function device may be a cellular phone, personal computer, laptop, workstation computer, or personal digital assistant that can be configured to an application to simulate programmer 20. Alternatively, a notebook computer, tablet computer, or other personal computer may execute an application to function as programmer 20, e.g., with a wireless adapter connected to the personal computer for communicating with IMD 12.

When programmer 20 is configured for use by the clinician, programmer 20 may be used to transmit initial programming information to IMD 12. This initial information may include hardware information for system 10 such as the type of catheter 14, the position of catheter 14 within patient 1, the type of therapeutic agent(s) delivered by IMD 12, a baseline orientation of at least a portion of IMD 12 relative to a reference point, therapy parameters of therapy programs stored within IMD 12 or within programmer 20, and any other information the clinician desires to program into IMD 12.

A clinician uses programmer 20 to program IMD 12 with one or more therapy programs that define the therapy delivered by IMD 12. During a programming session, the clinician may determine one or more therapy programs, which may include one or more therapy schedules, programmed doses, dose rates of the programmed doses, and specific times to deliver the programmed doses that may provide effective therapy to patient 1. Patient 1 may provide feedback to the clinician as to the efficacy of a specific therapy program being evaluated or desired modifications to the therapy program.

In some cases, programmer 20 may be configured for use by patient 1. When configured as the patient programmer, programmer 20 may have limited functionality in order to prevent patient 1 from altering critical functions or that are detrimental to patient 1. In this manner, programmer 20 may only allow patient 1 to adjust certain therapy parameters or set an available range for a particular therapy parameter. In some cases, a patient programmer may permit the patient to control IMD 12 to deliver a supplemental, patient bolus, if permitted by the applicable therapy program administered by the IMD, e.g., if delivery of a patient bolus would not violate a lockout interval or maximum dosage limit. Programmer 20 may also provide an indication to patient 1 when therapy is being delivered or when IMD 12 needs to be refilled or when the power source within programmer 20 or IMD 12 needs to be replaced or recharged.

Whether programmer 20 is configured for clinician or patient use, programmer 20 may communicate to IMD 12 or any other computing device via wireless communication. Programmer 20, for example, may communicate via wireless communication link 22 with IMD 12 using any of a number of radio frequency (RF) telemetry techniques. Programmer 20 may also communicate with another programmer or computing device via a wired or wireless connection using any of a variety of local wireless communication techniques, such as RF communication according to one or more specification sets, such as the Medical Implant Communication Service (MICS) specification set, Medical Implant Telemetry System (MITS), Medical Data Service (MEDS), 802.11, or Bluetooth specification sets, infrared (IR) communication, or other standard or proprietary telemetry protocols. Programmer 20 may also communicate with another programmer or computing device via exchange of removable media, such as magnetic or optical disks, or memory cards or sticks. Further, programmer 20 may communicate with IMD 12 and another programmer via remote telemetry techniques, communicating via a local area network (LAN), wide area network (WAN), public switched telephone network (PSTN), or cellular telephone network, for example.

Figure 2:
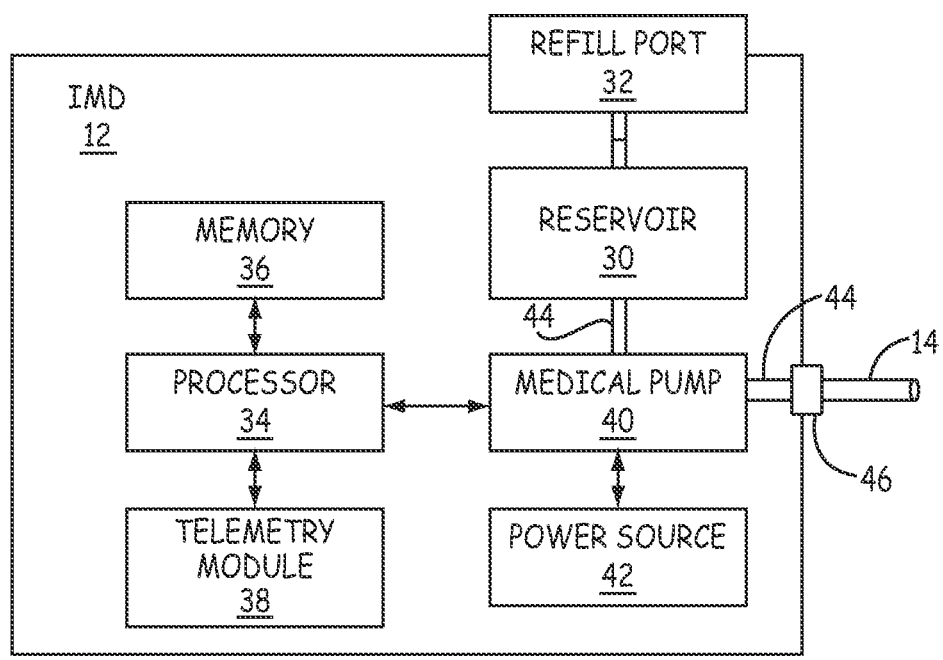
FIG. 2 is functional block diagram illustrating an example fluid delivery device.

FIG. 2 is a functional block diagram illustrating components of an example of IMD 12. The example IMD 12 shown in FIG. 2 includes reservoir 30, refill port 32, processor 34, memory 36, telemetry module 38, medical pump 40, power source 42, internal channels 44, and catheter access port 46.

Refill port 32 may comprise a self-sealing injection port. The self-sealing injection port may include a self-sealing membrane to prevent loss of therapeutic agent delivered to reservoir 30 via refill port 32. After a delivery system, e.g., a hypodermic needle, penetrates the membrane of refill port 32, the membrane may seal shut when the delivery system is removed from refill port 32. Internal channels 44 comprises one or more segments of tubing or a series of cavities that run from reservoir 30, around or through medical pump 40 to catheter access port 46.

Processor 34 controls the operation of medical pump 40 with the aid of software instructions associated with program information that is stored in memory 36. In one example, processor 34 is configured to run the software instructions in order to control operation of IMD 12. For example, the software instructions may define therapy programs that specify the amount of a therapeutic agent that is delivered to a target tissue site within patient 1 from reservoir 30 via catheter 14, e.g., dose, the rate at which the agent is delivered, e.g., dosage rate, and the time at which the agent will be delivered and the time interval over which the agent will be delivered, e.g., the therapy schedule for dose or doses defined by program. In other examples, a quantity of the therapeutic agent may be delivered according to one or more physiological characteristics of a patient, e.g., physiological characteristics sensed by one or more sensors (not shown) implanted within a patient as part of therapy system 10 (FIG. 1). Processor 34 can include one or more processors, including one or more microprocessors, digital signal processors (DSPs), application specific integrated circuits (ASICs), field programmable gate arrays (FPGAs), or any other equivalent integrated or discrete logic circuitry, as well as any suitable combination of such components. The term "processor" or "processing circuitry" may generally refer to any of the foregoing logic circuitry, alone or in combination with other logic circuitry, or any other equivalent circuitry.

Memory 36 may include any volatile or non-volatile media, such as a random access memory (RAM), read only memory (ROM), non-volatile RAM (NVRAM), electrically erasable programmable ROM (EEPROM), flash memory, and the like. As mentioned above, memory 36 may store program information including instructions for execution by processor 34, such as, but not limited to, therapy programs, historical therapy programs, timing programs for delivery of the therapeutic agent from reservoir 30 to catheter 14, and any other information regarding therapy of patient 1. Memory 36 may include separate memory portions for storing instructions, patient information, therapy parameters (e.g., grouped into sets referred to as "dosing programs"), therapy adjustment information, program histories, and other categories of information such as any other data that may benefit from separate physical memory modules.

Telemetry module 38 in IMD 12, as well as telemetry modules in programmers, such as external programmer 20, may accomplish communication by RF communication techniques. In addition, telemetry module 38 may communicate with programmer 20 via proximal inductive interaction of IMD 12 with external programmer 20. Processor 34 controls telemetry module 38 to send and receive information.

Power source 42 delivers operating power to various components of IMD 12. Power source 42 may include a small rechargeable or non-rechargeable battery and a power generation circuit to produce the operating power. In the case of a rechargeable battery, recharging may be accomplished through proximal inductive interaction between an external charger and an inductive charging coil within IMD 12 (not shown). In some examples, power requirements may be small enough to allow IMD 12 to utilize patient motion and implement a kinetic energy-scavenging device to trickle charge a rechargeable battery.

Medical pump 40 may be a mechanism that delivers a therapeutic agent in a metered manner to target site 2 within patient 1 from reservoir 30 via catheter 14. Medical pump 40 may be a varieties of pumping mechanisms, including a peristaltic, piston, or other small size pumps suitable for use in an implantable medical device. Medical pump 40 may include an actuation mechanism that is electrically energized to provide a pump stroke to move fluid from reservoir 30. The actuation mechanism may comprise an electromagnetic coil and an actuator that is movable in response to electrical energization of the coil. Other actuation mechanisms may be used, such as a piezoactuator.

Figure 3:
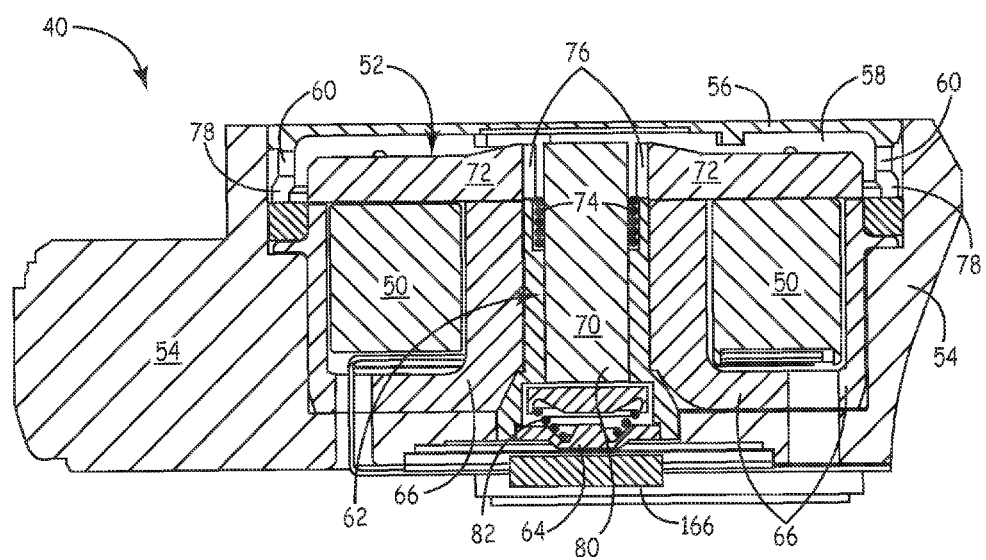
FIG. 3 is a sectional view of an example pump for use in the fluid delivery device of FIG. 1.

FIG. 3 is a sectional view of an example of medical pump 40 including electromagnetic coil 50, actuator 52, bulkhead 54, and cover 56. During the operation of medical pump 40, the therapeutic agent flows from reservoir 30 into chamber 58 formed within bulkhead 54. In one example, the therapeutic agent enters chamber 58 through holes 60 in cover 56. Once within chamber 58, the therapeutic agent enters central aperture 62 and is pushed by the motion of actuator 52 through one-way valve 64. After passing through one-way valve 64, the therapeutic agent is directed through internal channels 44 to catheter 14 and onto to one or more target sites within the patient.

Electromagnetic coil 50 comprises one or more insulated conductors arranged in a multitude of turns. As examples, electromagnetic coil 50 may include a single continuous conductor or more than one conductor electrically connected in series or in parallel. Current is delivered to electromagnetic coil 50 to produce a magnetic field that moves actuator 52 through a pump stroke from a rearward position (upward in FIG. 3) to a forward position (downward in FIG. 3). In one example, electromagnetic coil 50 is retained in a magnetic cup 66 that includes a highly magnetic material that efficiently magnetizes in response to current through electromagnetic coil 50. As an example, magnetic cup 66 may include a highly magnetic steel alloy, such as a highly magnetic stainless steel alloy, for example 430F stainless steel.

In the example shown in FIG. 3, actuator 52 includes a piston 70 and an armature 72. Actuator 52 is positioned such that piston 70 is located within central aperture 62. A spring 74 is located within central aperture 62 adjacent armature 72. Spring 74 biases actuator 52 into a rearward position away from coil 50 (upward as shown in FIG. 3). Armature 72 is made from a magnetic material, such as a stainless steel. When coil 50 and magnetic cup 66 are magnetized, armature 72 is attracted to and moves toward magnetic cup 66 so that actuator 52 moves to a forward position (downward as shown in FIG. 3), producing a pump stroke. The magnetic attraction force between armature 72 and magnetic cup 66 overcomes the force of spring 74 to move actuator 52 through a pump stroke from the rearward position to forward position (downward in FIG. 3) to create a pumping action of piston 70. The motion of piston 70 forces the therapeutic agent within central aperture 62 and adjacent to a distal end 80 of piston 70 through one-way valve 64.

In one example, the therapeutic agent flows through holes 60 formed in cover 56 into chamber 58, through holes 76 in armature 72 and/or around armature 72 through a gap between armature 72 and a sidewall 78 of cover 56 and into central aperture 62, where the therapeutic agent is forced out one-way valve 64 by piston 70 when actuator 52 is driven from the rearward position to the forward position. Because armature 72 is within the therapeutic agent flow path, the material of armature 72 should resist corrosion, such as a magnetic stainless steel alloy that is corrosion resistant, such as AL29-4 stainless steel.

Following a pump stroke, current through electromagnetic coil 50 is stopped, and spring 74 biases actuator 52 into its original rearward position with armature 72 pushed against cover 56. As spring 74 moves actuator 52 into the rearward position, the therapeutic agent flows through a small gap between piston 70 and central aperture 62 to fill the growing space within central aperture 62 between distal end 80 of piston 70 and one-way valve 64. While some of the therapeutic agent may flow back through the gap between piston 70 and central aperture 62 during a pump stroke, the speed of piston 70 during a pump stroke combined with the viscosity of the therapeutic agent generally makes any amount of the therapeutic agent flowing back through the gap between piston 70 and the inner surface of central aperture 62 during a pump stroke negligible.

The therapeutic agent pushed by piston 70 during a pump stroke exits medical pump 40 through one-way valve 64. In one example, one-way valve 64 includes a spring 82 that biases one-way valve 64 into a closed position when actuator 52 is not being driven forward. When actuator 52 is driven from the rearward position to the forward position, as described above, the force of the therapeutic agent being pushed forward counteracts the force of spring 82 and opens one-way valve 64 so that the therapeutic agent can flow through one-way valve 64. The configuration of one-way valve 64 may be referred to as a lift check valve. In other examples, different valve configurations may be used including, but not limited to, ball check valves, diaphragm valves, gate valves and other valves. Generally, one-way valve 64 should be selected to minimize a pressure differential in the therapeutic agent flow path at one-way valve 64 while maintaining a fluid seal except during pump strokes.

Piston 70 may be interference fit to armature 72 or secured to armature 72 by other suitable techniques. Like armature 72, piston 70 is located within the therapeutic agent flow path and should resist corrosion. In one example, piston 70 comprise a sapphire material, which resists corrosion and limits wear between piston 70 and central aperture 62 caused by the pumping action of medical pump 40. Piston 70 may comprise other materials, however, such as a metal material, for example a stainless steel or titanium alloy. In some examples, actuator 52 may comprise a unitary component wherein piston 70 and armature 72 comprise a single magnetic material such as a stainless steel alloy.

Further examples of medical pumps that may be used in IMD 12 are disclosed in U.S. Provisional Patent Application Ser. No. 61/174,457, filed on Apr. 30, 2009, the disclosure of which is incorporated herein by reference in its entirety.

Figure 4:
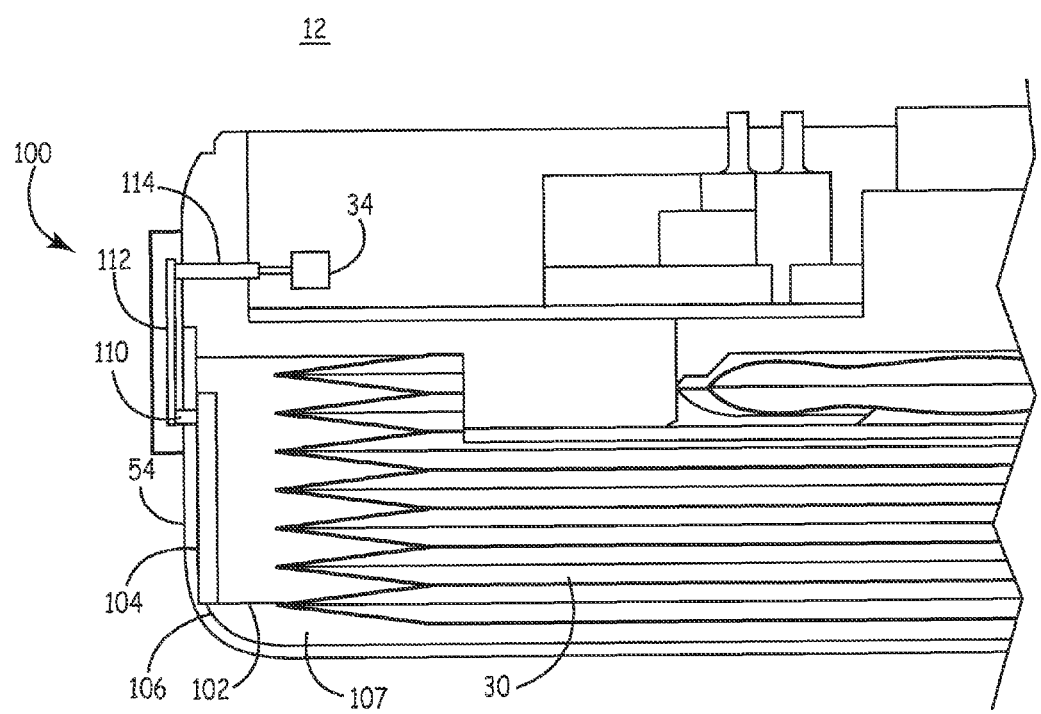
FIG. 4 a sectional view of one reservoir fill status detector of the present invention.

FIG. 4 illustrates one embodiment of a reservoir fill level detector 100 of the present invention for utilization in IMD 12. The reservoir fill level detector 100 provides an indication of the volume of drug contained within the reservoir 30 of the IMD 12. The reservoir fill level detector 100 may include a contact pad 102 placed at the bottom outer edge of the reservoir 30 that is in contact with a resistor strip 104 mounted onto an inner wall 106 of a propellant chamber 107. The propellant chamber 107 is secured in a pump bulkhead 54 that generally retains, supports, and encloses the components of the IMD 12. Some exemplary components that may be secured in the bulkhead 54 include the power source (not shown), the pump (not shown), and other components as earlier discussed. In one embodiment the reservoir 30 is grounded to bulkhead 54.

As illustrated, the propellant chamber 107 may be formed by a cover or other structure that is mounted to the bulkhead 54 (not shown) and forms the propellant chamber 107. The reservoir 30 is contained in the propellant chamber 107. A propellant fills the area of the propellant chamber 107 between the reservoir 30 and the inner wall 106 and maintains a constant desired pressure around the reservoir 30. Maintaining the desired pressure around reservoir 30 may aid in expelling the therapeutic agent from the reservoir 30 and to the pump 40.

The strip 104 is connected to feed thru 110 which in turn is connected to wire 112. Wire 112 may travel on the inside or the outside of the bulkhead 54 and is connected through another feed thru 114 to electronic processor 34 or other electronic circuitry that can measure the resistance across the circuit. The circuit is completed by grounding the reservoir 30. In alternative embodiments, the circuit is completed by attaching another conductive wire to the reservoir and back to the processor 34.

The contact pad 102 may be any suitable conductor that can be formed into a desired shape and retain a desired stiffness. Suitable materials may include non-magnetic resistance wire such as a nickel chromium iron alloy wire, nickel on a flexible strip, or a carbon-impregnated elastomer. The contact pad 102 completes the circuit between the strip 104 and the grounded reservoir 30. The strip 104 may be any suitable resistive material, including the same materials that form the contact pad 102. It may be desirable to form strip 104 of a material that provides low wear, flexibility, low contact resistance, and an easy manner of affixing to the reservoir. In one embodiment the strip 104 may be titanium. Additional materials for the strip may include nickel chromium alloy, nickel on a strip, carbon impregnanted polymer. The resistance of strip 104 may be any resistance desired, but may include a resistance between 100 and 10 k ohms per inch. In one embodiment the strip 104 is a wire wound around a fiberglass, ceramic, or plastic core. In further embodiments the resistor may be a single wire placed on a laminate, a foil resistor, a thick film resistor or a thin film resistor. The strip 104 may be insulated from the bulkhead 54 by any suitable insulator with the feed thru 110 connecting the strip 104 and the wire 112.

During use, an electric current is passed through the reservoir fill level detector 100. The current may be on the order of micovolts or millivolts. During the filling or emptying of the reservoir 30, the contact pad 102 changes its point of contact with the strip 104 and thereby changes the overall resistance of the system. The electrical resistance of the system is directly related to the position of the reservoir 30 and therefore the fill status of the reservoir. The processor 34 monitors the resistance of the electrical circuit and determines the fill status of the reservoir 30.

In one embodiment, the processor 34 has preprogrammed information stored regarding the total expected resistance when the reservoir 30 is at different fill levels. The processor 34 may compare the resistance at any given time with the known values to determine the fill level. In other embodiments, the processor 34 may send the resistance information through the telemetry module 38 to the programmer 20 whereby programmer 20 determines the fill level. In further embodiments, the reservoir fill level detector 100 may be calibrated manually when requested or automatically during the refill procedure. In one embodiment, the clinician may indicate to the processor 34 when the reservoir 30 is at an empty or full state whereby the processor 34 may take a resistance check and recalibrate the empty or fill state resistance. Several different methods of processing the resistance information may be utilized to arrive at a fill level without changing the scope of the present invention.

As may be appreciated, the contact pad 102 may be connected to the reservoir 30 at any desired position as long as the contact pad 102 maintains an operable connection to the strip 104. Placement of the contact pad 102 at the bottom of the reservoir 30, however, allows for the greatest travel of the contact pad 102 along the strip 104 and therefore may provide a greater range of resistances to be measured to determine the reservoir 30 fill status.

The reservoir fill level detector 100 may be utilized at regular intervals to check the fill level of the reservoir 30. In other embodiments, a user or clinician may manually initiate the reservoir fill level detector 100 to check the fill status of the reservoir 30 at anytime. In further embodiments, the reservoir fill level detector 100 is initiated automatically or manually during a filling procedure. The reservoir fill level detector 100 may report continual reservoir fill level information during a filling or emptying procedure. In other embodiments, a patient programmer may be utilized to determine the reservoir fill level.

Placement of the contact pad 102 on the reservoir 30 and in relation to strip 104 should be accomplished in a manner that does not result in periods of disconnect during the expansion and contraction of the reservoir 30. The contact pad 102 should transverse a known path along strip 104 during expansion and contraction of the reservoir 30. In addition, the interaction between the contact pad 102 and strip 104 should not present any possibility of restricting movement of the reservoir. Because the number of empty-fill cycles during the life of the pump is relatively low, wear due to mechanical contact between the contact pad 102 and strip 104 should not be a significant problem over the life of the IMD 12.

Figure 5A:
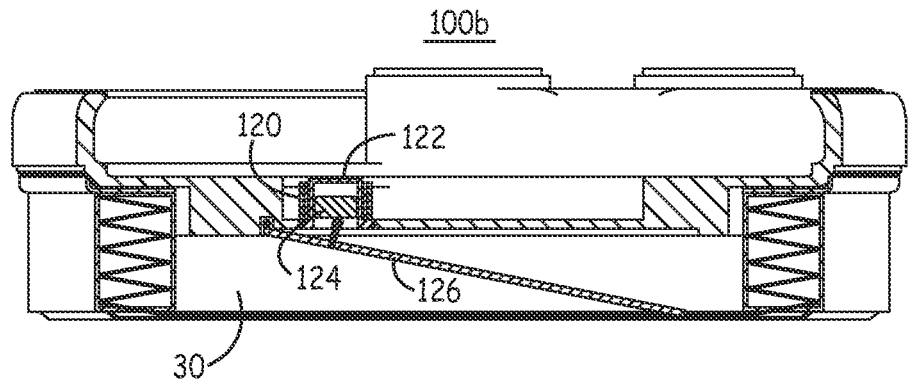
FIG. 5A is another embodiment of a reservoir fill status detector of the present invention.
Figure 5B:
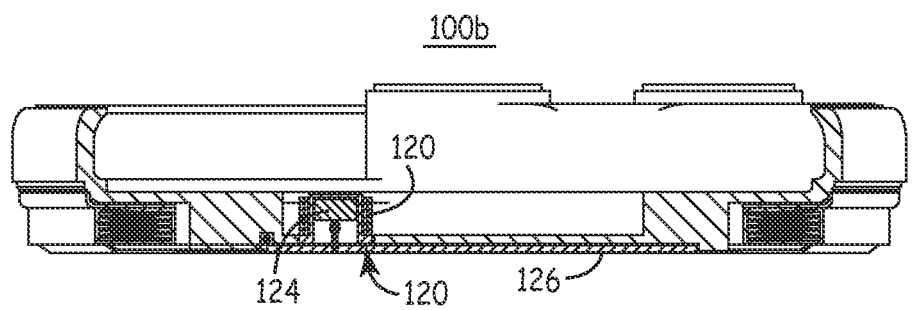
FIG. 5B is another view of the reservoir fill status detector of FIG. 5A.
Figure 5C:
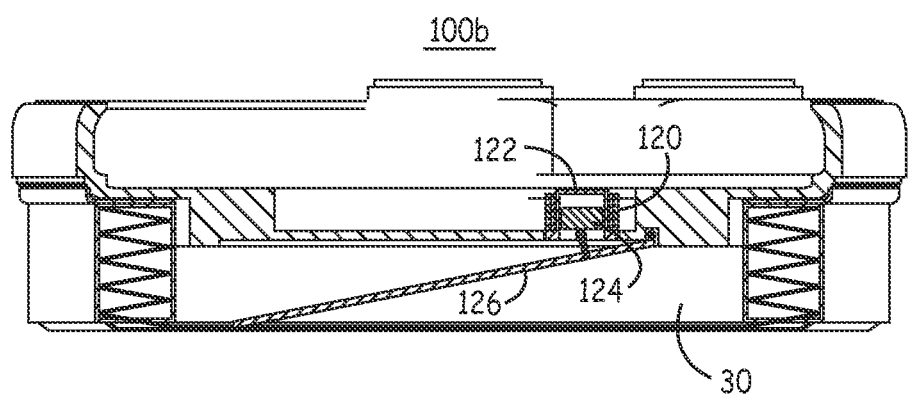
FIG. 5C is another view of the reservoir fill status detector of FIG. 5A.

FIGS. 5A through 5C illustrate another embodiment of a reservoir fill level detector 100b of the present invention. The reservoir fill level detector 100b includes a coil 120 located in the bulkhead 54 of the pump above the propellant chamber 107. The coil 120 is electrically isolated from the propellant chamber 107 and the pump 40. A recess 122 in the propellant chamber 107 concentric with the coil 120 receives a magnetic block 124 that moves in and out of the recess 122. In the present embodiment, the magnetic block 124 is mounted on a lever arm 126. The lever arm 126 is hingedly attached to an upper portion of the propellant chamber 107. Movement of a bottom portion of the reservoir 30 moves the lever arm 126 and changes the position of the magnetic block 124 in the recess 122 and relative to the coil 120.

Coil 120 may be made of copper wire formed into a generally cylindrical coil or loop. In other embodiments, the coil 120 may be made with further materials, for example, electrical steel can be laminated into the design to prevent eddy currents. The coil 120 may be any diameter and height depending on the size and shape of the recess 122 and the requirements of the desired electric field.

Processor 34 or other circuit connected to the coil 120 measures the current through the coil 120. The position of the block 124 will cause a predictable change in the current passed through the coil 120. The processor 34 may record or interpret the information in combination with memory 36 to give a reservoir fill level based upon the measured current. In further embodiments, the measurements are calibrated as desired. In still further embodiments, the block 124 may be charged and the coil 122 used to detect the position of the block 124.

Attachment of the magnetic block 124 to the lever arm 126 may allow for a selectable range of motion of the magnetic block 124 in the coil 120. The change in the current in coil 120 caused by the relative positions of the magnetic block 124 may be monitored by the processor 34 and the information sent by the telemetry module 38 to the programmer 20.

The magnetic block 124 can take any shape that fits comfortably into the recess 122 and affects the coil 120 in a measurable and predictable way. In one embodiment, the magnetic block 124 is a ferrous material, such as A129-4. Other types of ferromagnetic materials may also be used, such as materials made of one or more of cobalt, iron, nickel, manganese, and other ferromagnetic materials known in the art. In further embodiments, the magnetic block 124 may be formed of a ferromagnetic material that is covered in a material known to be suitable for contact with therapeutic agents, such as stainless steel or various polymers. It is important that all of the components of the reservoir fill detector 100b exposed to the therapeutic agent are inert to the same.

As may be appreciated, the relative placement of the coil 120, lever arm 126 and magnetic block 124 can be changed and alternated in a variety of ways. For example, the coil 120 may be positioned substantially in the confines of the reservoir 30 as long as the coil is isolated from the therapeutic fluid. In such an embodiment a feed thru may be required to supply electric power to the coil 120. The lever arm 126 and the magnetic block 124 would operate substantially the same as previously described but not engage the bumped out recess 122 but a structure integrated into the reservoir. In another configuration the magnetic block 124 may be the stationary piece and the coil 122 may be mounted on the lever. In still another alternative embodiment, the lever arm 126 may be hingedly attached to the bottom of the propellant chamber 107 wherein the lever arm 126 is biased against the bottom of the reservoir 30 and the coil 120 is placed along an outer edge of the bulkhead 54.

Figure 6A:
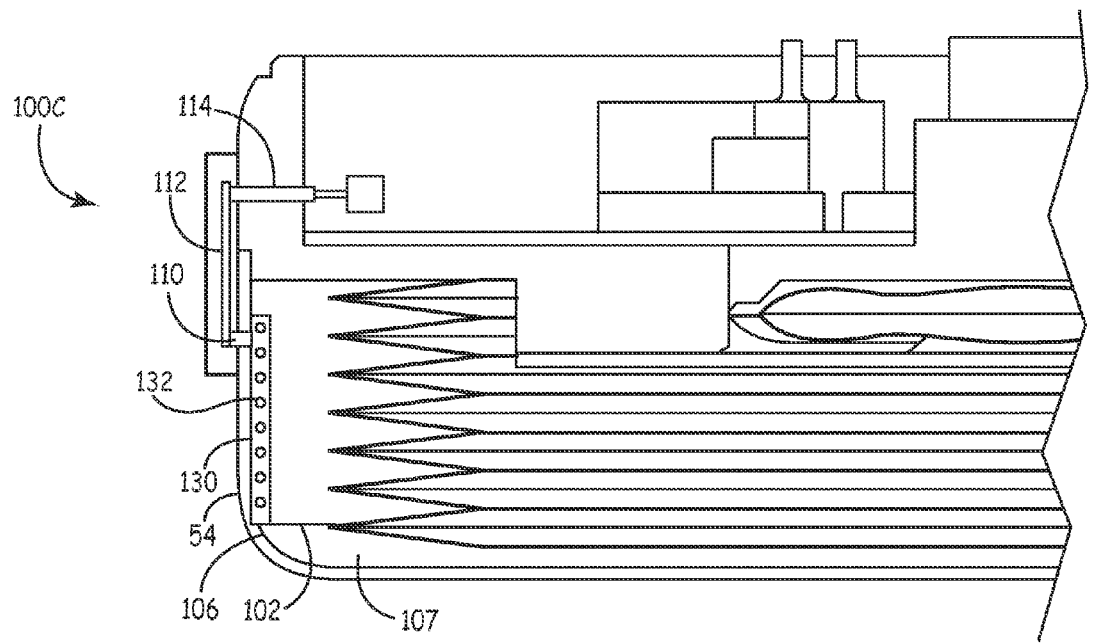
FIG. 6A is a sectional view of another embodiment of a reservoir fill status detector of the present invention.
Figure 6B:
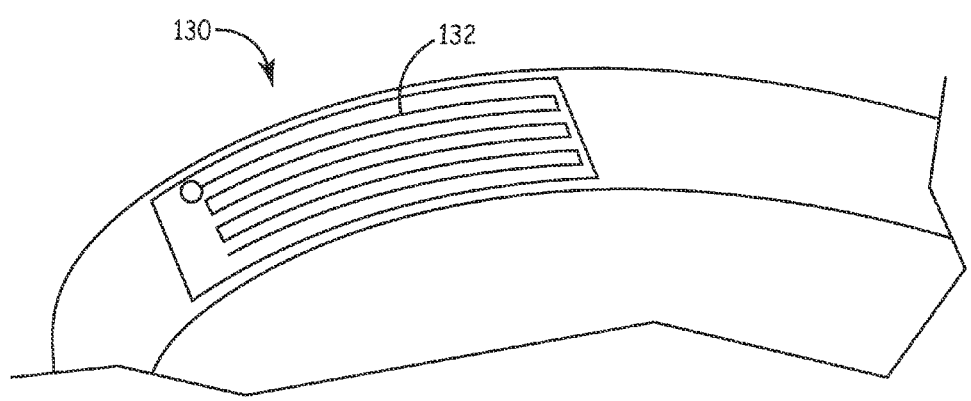
FIG. 6B is another view of a portion the reservoir fill status detector of FIG. 5A.

FIGS. 6A and 6B illustrate another embodiment reservoir fill level detector 100c. The reservoir fill level detector 100c includes substantially the same components as reservoir fill level detector 100, including a contact pad 102, an inner wall 106 of a propellant chamber 107 that is secured in a bulkhead 54, a feed thru 110 connected to a wire 112, and a second feed thru 114 allowing wire 112 to connect with processor 34. In the present embodiment, a flex circuit 130 replaces the strip 104. The flex circuit 130 is mounted on the inner wall 106 of the propellant chamber 107. The flex circuit 130 is insulated from the bulkhead and includes a patterned resistor 132. The contact pad 102 operably contacts the flex circuit 130 along a desired axis whereby the contact pad 102 makes electrical contact with one or more parts of patterned resistor 132 depending on the position of the reservoir 30. The position of the contact pad 102 on the resistor 132 of flex circuit 130 provides for known resistances which are detectable by processor 34 or other designated circuits. Rather than providing a continuously variable signal, as with fill level detector 100, fill level detector 100c provides a number of set resistance changes when the contact pad 102 transitions from one point on the patterned resistor 132 to another point. Each point on the patterned resistor 132 relates to a known position of contact pad 102 and therefore a known fill status of reservoir 30. As may be appreciated, the flex circuit 130 may be manufactured in a number of different ways, include a variety of different conductive and non-conductive materials, and include a variety of patterns for the resistor 132. The materials utilized, however, should be inert and not interfere with the propellant that resides in propellant chamber 107.

As may be appreciated, the reservoir fill level detector 100, 100b, and 100c may require the use of electrical energy from the battery. As such, the energized portions of the fill level detector 100, 100b may be set into a default 'off' state such that extra energy is not drained from the battery. Rather, the reservoir fill level detector 100, 100b, and 100c may be energized and report the fill level of the reservoir 30 when actively queried by the clinician through use of the programmer 20. The reservoir fill level detector 100, 100b, and 100c may be also energized when a needle is detected in the refill port or when a pressure sensor (not shown) detects fluid flowing into or out of the refill port or the reservoir. In still further embodiments, the reservoir fill level detector 100, 100b, and 100c may be on a programmed interval to check the level of the reservoir 30 and to determine if a low fill status alarm should be activated. The reservoir fill level detector 100, 100b, and 100c may also be initiated to determine fill status through the user's programmer. In one example, IMD 12 may include an alarm component that is configured to produce an audible alarm sound when the volume drops below a certain threshold level.

Although the target therapy delivery site described with reference to the foregoing examples is proximate to the spinal cord of a patient, other applications of therapy systems in accordance with this disclosure include alternative delivery sites. In some examples, the target delivery site may be proximate to different types of tissues including, e.g., nerves, e.g. sacral, pudendal or perineal nerves, organs, muscles or muscle groups. In one example, a catheter may be positioned to deliver a therapeutic fluid to a deep brain site or within the heart or blood vessels.

Delivery of a therapeutic fluid within the brain may help manage a number of disorders or diseases including, e.g., chronic pain, diabetes, depression or other mood disorders, dementia, obsessive-compulsive disorder, migraines, obesity, and movement disorders, such as Parkinson's disease, spasticity, and epilepsy. A catheter may also be positioned to deliver insulin to a patient with diabetes. In other examples, the system may deliver a therapeutic fluid to various sites within a patient to facilitate other therapies and to manage other conditions including peripheral neuropathy or postoperative pain mitigation, ilioinguinal nerve therapy, intercostal nerve therapy, gastric drug induced stimulation for the treatment of gastric motility disorders and/or obesity, and muscle stimulation, or for mitigation of peripheral and localized pain e.g., leg pain or back pain.

The techniques described in this disclosure, including those attributed to processor 34 of IMD 12 and external programmer 20 may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

This disclosure refers to illustrative examples that are not meant to be construed in a limiting sense. Various modifications of the illustrative examples, as well as additional examples of the disclosure, will be apparent to persons skilled in the art upon reference to this description. Any specific numerical value or range described in the foregoing disclosure shall not be limiting, except for values or ranges included in the following claims.

The invention claimed is:

1. A medical device system comprising:
  a reservoir configured to store a therapeutic fluid, the reservoir positioned in a chamber; and
  a reservoir fill level detector configured to detect a fill status of the reservoir, the reservoir fill level detector further comprising:
  a contact pad operably attached to the reservoir whereby the contact pad is attached to a bottom side of the reservoir and moves, in response to movement of the bottom side of the reservoir, in a predetermined path during the emptying and filling of the reservoir;
  a resistor strip mounted on the inside of the chamber whereby the resistor strip is in continual contact with the contact pad along the entire predetermined path;
  an energy source for providing a current along the resistor strip whereby the total resistance of the resistor strip is variable depending on the position of the contact pad; and a processor configured to monitor the resistance of the resistor strip.

2. The system of claim 1, wherein the processor utilizes the resistance of the resistor strip to determine a fill status of the reservoir.

3. The system of claim 1 wherein the contact pad is formed one or more of nickel, chromium, titanium, niobium and iron.

4. The system of claim 1 wherein the reservoir is electrically grounded.

5. The system of claim 1, wherein the processor compares the monitored resistance to predetermined resistance information to determine the fill status.

6. The system of claim 5, wherein the processor is operably connected to a memory containing the predetermined resistance information.

7. The system of claim 6, wherein the predetermined resistance information is determined by calibrating the resistance during a known fill state of the reservoir.

8. The system of claim 1, wherein resistor strip is a wound resistor.

9. The system of claim 1, wherein the resistor strip is one of a wire, metal foil, thick film, thin film, or carbon film resistor on an insulated backing.

10. The system of claim 1, wherein the resistor strip is electrically insulated from the chamber.

11. The system of claim 1, wherein the resistance is communicated to an external programmer whereby the external programmer determines the fill status of the reservoir.

* * * * *